United States Patent
Hashimoto et al.

(10) Patent No.: US 8,283,053 B2
(45) Date of Patent: Oct. 9, 2012

(54) FLUORANTHENE DERIVATIVE AND ORGANIC LIGHT EMITTING DEVICE HAVING THE SAME

(75) Inventors: Masashi Hashimoto, Tokyo (JP); Akihito Saitoh, Yokohama (JP); Naoki Yamada, Inagi (JP); Satoshi Igawa, Fujisawa (JP); Jun Kamatani, Tokyo (JP); Takao Takiguchi, Chofu (JP); Shinjiro Okada, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 220 days.

(21) Appl. No.: 12/298,739

(22) PCT Filed: Apr. 24, 2007

(86) PCT No.: PCT/JP2007/059351
§ 371 (c)(1),
(2), (4) Date: Oct. 27, 2008

(87) PCT Pub. No.: WO2007/126112
PCT Pub. Date: Nov. 8, 2007

(65) Prior Publication Data
US 2009/0102371 A1    Apr. 23, 2009

(30) Foreign Application Priority Data
Apr. 27, 2006 (JP) .................................. 2006-123783
Feb. 22, 2007 (JP) .................................. 2007-042663

(51) Int. Cl.
H01L 51/54 (2006.01)
C07C 13/32 (2006.01)
C07D 403/02 (2006.01)
C07D 471/02 (2006.01)

(52) U.S. Cl. .......... 428/690; 428/917; 313/504; 585/27; 544/347; 546/94; 548/418

(58) Field of Classification Search .................... None
See application file for complete search history.

(56) References Cited

U.S. PATENT DOCUMENTS

| | | | |
|---|---|---|---|
| 6,686,066 B2 * | 2/2004 | Kwon et al. | 428/690 |
| 2002/0022151 A1 | 2/2002 | Ishikawa et al. | 428/690 |
| 2003/0219625 A1 * | 11/2003 | Wolk et al. | 428/690 |
| 2007/0063189 A1 | 3/2007 | Schwalm et al. | 257/40 |
| 2007/0249878 A1 | 10/2007 | Iwawaki et al. | 585/27 |
| 2008/0124577 A1 | 5/2008 | Saitoh et al. | 428/704 |
| 2008/0278065 A1 * | 11/2008 | Ueda et al. | 313/504 |

FOREIGN PATENT DOCUMENTS
JP    11-149987    6/1999
(Continued)

OTHER PUBLICATIONS

Machine generated translation for JP 11-149987, which was published Jun. 1999.*
Partial machine-generated translation for JP 2004043349, which was published Feb. 2004.*
(Continued)

*Primary Examiner* — Dawn L. Garrett
(74) *Attorney, Agent, or Firm* — Fitzpatrick, Cella, Harper & Scinto

(57) ABSTRACT

To provide a high-performance organic light emitting device and a novel compound possessed by the device. Provided are a novel fluoranthene derivative and an organic light emitting compound having the derivative.

6 Claims, 3 Drawing Sheets

FOREIGN PATENT DOCUMENTS

| | | |
|---|---|---|
| JP | 2001-257074 | 9/2001 |
| JP | 2001-267079 | 9/2001 |
| JP | 2001-307883 | 11/2001 |
| JP | 2002-043058 | 2/2002 |
| JP | 2002-069044 | 3/2002 |
| JP | 2004-43349 * | 2/2004 |
| JP | 2005-240008 | 9/2005 |
| JP | 2005-240008 A | 9/2005 |
| JP | 2005-240011 | 9/2005 |
| WO | 2004/020372 A1 | 3/2004 |
| WO | WO 2005/026088 A2 | 3/2005 |
| WO | WO 2005044942 A1 * | 5/2005 |

OTHER PUBLICATIONS

Ricky J. Tseng et al., "Highly Efficient 7, 8, 10-Triphenylfluoranthene-doped Blue Organic Light-Emitting Diodes for Display Application," Applied Physics Letters, vol. 88, pp. 093512-1 to 093512-3, (Mar. 2006).

Japanese Office Action issued in corresponding Application No. 2007-042663 dated May 27, 2011; 9 pages; and English translation thereof.

Chinese Office Action issued in corresponding application No. 200780014776.7 dated Jul. 25, 2011—8 pages and English translation thereof.

* cited by examiner

FLUORANTHENE DERIVATIVE AND ORGANIC LIGHT EMITTING DEVICE HAVING THE SAME

TECHNICAL FIELD

The present invention relates to a light emitting device using an organic compound.

BACKGROUND ART

Recent progress in an organic light emitting device is remarkable. The organic light emitting device has such characteristics that it can be made into a thin, lightweight light emitting device which: provides high luminance at a low applied voltage; and has the diversity of a luminous wavelength and high-speed responsiveness. The characteristics suggest that the light emitting device may be used in a wide variety of applications.

However, the conventional organic light emitting device requires optical output with additionally high luminance or high conversion efficiency. In addition, the organic light emitting device still involves many problems in terms of durability such as a change with time due to long-term use and deterioration due to, for example, an atmospheric gas containing oxygen or humidity. Further, when it is attempted that the device is applied to a full-color display, each of blue light, green light, and red light must be emitted at a good color purity. However, problems concerning the light emission have not been sufficiently solved yet.

In addition, a large number of aromatic compounds and fused ring aromatic compounds as fluorescent organic compounds for use in, for example, an electron transporting layer and a light emitting layer have been researched. However, it is hard to say that a compound capable of sufficiently satisfying light emission luminance and durability has been obtained.

In addition, examples of a patent document concerning a compound having a fluoranthene skeleton related to the present invention include Japanese Patent Application Laid-Open No. H11-149987, Japanese Patent Application Laid-Open No. 2001-307883, International Publication No. WO 2005/026088, Japanese Patent Application Laid-Open No. 2005-240008, and Japanese Patent Application Laid-Open No. 2005-240011.

DISCLOSURE OF THE INVENTION

An object of the present invention is to provide a compound formed of a molecular structure containing at least two identical fused ring aromatic groups each of which: is tricyclic or more; and has at least one fused ring structure at any one of 1- to 10-positions of novel fluoranthene adjacent to a position at which fluoranthene is substituted by the group.

Another object of the present invention is to provide an organic light emitting device using the above compound and having an optical output with extremely high efficiency and extremely high luminance. Another object of the present invention is to provide an organic light emitting device having extremely high durability. Another object of the present invention is to provide an organic light emitting device that can be easily produced at a relatively low cost.

According to the present invention, there is provided a fluoranthene derivative represented by the following general formula (1):

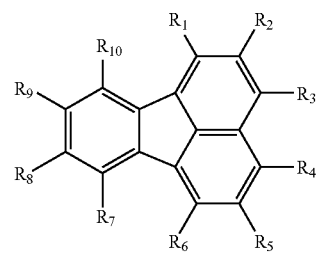

where:

$R_1$ to $R_{10}$ are each independently selected from a hydrogen atom, a halogen atom, a substituted amino group, a linear or branched alkyl group in which one methylene group may, or two or more methylene groups not adjacent to each other may each, be substituted by —O— or —CH=CH—, and in which a hydrogen atom may be substituted by a fluorine atom, an aryl group which may have a substituent that represents a halogen atom, a nitro group, a substituted amino group, or a linear or branched alkyl group having 1 to 20 carbon atoms in which one methylene group may, or two or more methylene groups not adjacent to each other may each, be substituted by —O— or —CH=CH—, and in which a hydrogen atom may be substituted by a fluorine atom, or a heterocyclic group which may have a substituent that represents a halogen atom, a nitro group, a substituted amino group, or a linear or branched alkyl group having 1 to 20 carbon atoms in which one methylene group may, or two or more methylene groups not adjacent to each other may each, be substituted by —O— or —CH=CH—, and in which a hydrogen atom may be substituted by a fluorine atom; and at least two of $R_1$ to $R_{10}$ represent identical fused ring aromatic groups each of which is represented by a general formula (2), is tricyclic or more, and has at least one fused ring structure at a position adjacent to a position at which the group is bonded to a fluoranthene ring:

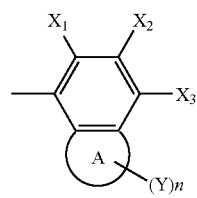

where:

n represents an integer of 2 or more, and plural Y's may be identical to or different from each other;

X and Y each represent a substituent, and $X_1$ to $X_3$ and Y are each independently selected from a hydrogen atom, a halogen atom, a substituted amino group, a linear or branched alkyl group in which one methylene group may, or two or more methylene groups not adjacent to each other may each, be substituted by —O— or —CH=CH—, and in which a hydrogen atom may be substituted by a fluorine atom, an aryl group which may have a substituent that represents a halogen atom, a nitro group, a substituted amino group, or a linear or branched alkyl group having 1 to 20 carbon atoms in which one methylene group may, or two or more methylene groups not adjacent to each other may each, be substituted by —O— or —CH=CH—, and in which a hydrogen atom may be substituted by a fluorine atom, or a heterocyclic group which may have a substituent that represents a halogen atom, a nitro group, a substituted amino group, or a linear or branched alkyl group having 1 to 20 carbon atoms in which one methylene group may, or two or more methylene groups not adjacent to each other may each, be substituted by —O— or —CH=CH—, and in which a hydrogen atom may be substituted by a fluorine atom; and X and Y may form a ring structure.

According to the present invention, there can be provided a novel, excellent fluoranthene derivative. In addition, an organic light emitting device having such novel fluoranthene derivative can emit light with high luminance at a low applied voltage, and is excellent in durability. In particular, an organic light emitting device using the fluoranthene derivative as a guest for its light emitting layer can emit light with high luminance at a low applied voltage, and is excellent in durability.

BEST MODE FOR CARRYING OUT THE INVENTION

Figure 1:
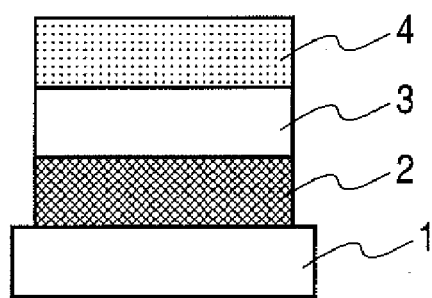
FIG. 1 is a sectional view showing an example of an organic light emitting device in the present invention.

The present invention relates to a fluoranthene derivative represented by the following general formula (1):

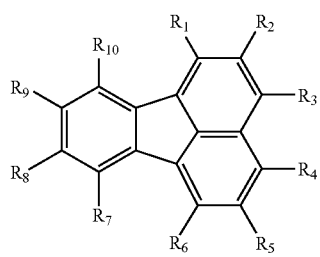

(1)

where:
$R_1$ to $R_{10}$ are each independently selected from
a hydrogen atom,
a halogen atom,
a substituted amino group,
a linear or branched alkyl group in which one methylene group may, or two or more methylene groups not adjacent to each other may each, be substituted by —O— or —CH=CH—, and in which a hydrogen atom may be substituted by a fluorine atom, an aryl group which may have a substituent that represents a halogen atom, a nitro group, a substituted amino group, or a linear or branched alkyl group having 1 to 20 carbon atoms in which one methylene group may, or two or more methylene groups not adjacent to each other may each, be substituted by —O— or —CH=CH—, and in which a hydrogen atom may be substituted by a fluorine atom, or a heterocyclic group which may have a substituent that represents a halogen atom, a nitro group, a substituted amino group, or a linear or branched alkyl group having 1 to 20 carbon atoms in which one methylene group may, or two or more methylene groups not adjacent to each other may each, be substituted by —O— or —CH=CH—, and in which a hydrogen atom may be substituted by a fluorine atom; and at least two of $R_1$ to $R_{10}$ represent identical fused ring aromatic groups each of which is represented by a general formula (2), is tricyclic or more, and has at least one fused ring structure at a position adjacent to a position at which the group is bonded to a fluoranthene ring:

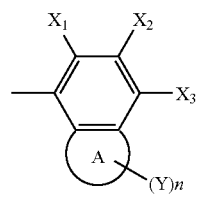

(2)

where:
n represents an integer of 2 or more, and plural Y's may be identical to or different from each other;

X and Y each represent a substituent, and $X_1$ to $X_3$ and Y are each independently selected from
a hydrogen atom,
a halogen atom,
a substituted amino group,
a linear or branched alkyl group in which one methylene group may, or two or more methylene groups not adjacent to each other may each, be substituted by —O— or —CH=CH—, and in which a hydrogen atom may be substituted by a fluorine atom, an aryl group which may have a substituent that represents a halogen atom, a nitro group, a substituted amino group, or a linear or branched alkyl group having 1 to 20 carbon atoms in which one methylene group may, or two or more methylene groups not adjacent to each other may each, be substituted by —O— or —CH=CH—, and in which a hydrogen atom may be substituted by a fluorine atom, or a heterocyclic group which may have a substituent that represents a halogen atom, a nitro group, a substituted amino group, or a linear or branched alkyl group having 1 to 20 carbon atoms in which one methylene group may, or two or more methylene groups not adjacent to each other may each, be substituted by —O— or —CH=CH—, and in which a hydrogen atom may be substituted by a fluorine atom; and X and Y may form a ring structure.

In addition, $R_3$ and $R_8$ in the general formula (1) represent the fused ring aromatic groups each of which is tricyclic or more.

In addition, the fused ring aromatic groups each of which is tricyclic or more each includes a fused polycyclic ring having a skeleton containing at least one five-membered ring.

In addition, a fluoranthene derivative includes fluorene including the fused ring aromatic groups each of which is tricyclic or more.

In addition, a fluoranthene derivative includes fluoranthene including the fused ring aromatic groups each of which is tricyclic or more.

Further, an organic light emitting device includes: an anode; a cathode; and an organic compound layer interposed between the anode and the cathode, in which the organic compound layer has the compound represented by the general formula (1).

In addition, an organic light emitting device includes a light emitting layer including the organic compound layer.

In addition, an organic light emitting device includes an electroluminescence device that emits light by applying a voltage between the pair of electrodes.

Hereinafter, the present invention will be described in detail.

Specific examples of a substituent on any one of $R_1$ to $R_{10}$ in the general formula (1) are shown below; provided that these examples are merely representative examples, and the present invention is not limited to them.

Examples of the halogen atom include fluorine, chlorine, bromine, and iodine. When a light emitting device is produced by employing a vacuum vapor deposition method, fluorine from which an improvement in property with which the derivative sublimates can be expected is preferable.

Examples of the linear or branched alkyl group includes a methyl group, an ethyl group, a normal propyl group, an isopropyl group, an normal butyl group, a tertiary butyl group, an octyl group, a cyclohexyl group, a methoxy group, and a trifluoro group.

From the viewpoints of conductive property and glass transition temperature, a methyl group, a t-butyl group, a cyclohexyl group, and a trifluoromethyl group are preferable, a methyl group, a t-butyl group, and a trifluoromethyl group are more preferable, and a methyl group and a t-butyl group are still more preferable.

Examples of the substituted amino group include a dimethylamino group, a diethylamino group, a dibenzylamino group, a diphenylamino group, a ditolylamino group, and a dianisolylamino group. From the viewpoints of conductive property and glass transition temperature, a dimethylamino group, a diphenylamino group, and a ditolylamino group are preferable, and a diphenylamino group and a ditolylamino group are more preferable.

Examples of the heterocyclic group and the aryl group which may have a substituent include a phenyl group, a biphenyl group, a terphenyl group, a fluorenyl group, a naphthyl group, a fluoranthenyl group, an anthryl group, a phenanthryl group, a pyrenyl group, a tetracenyl group, a pentacenyl group, a triphenylenyl group, a perylenyl group, a thienyl group, a pyrrolyl group, a pyridyl group, a pyrazyl group, a pyrimidyl group, a pyridazinyl group, a quinolyl group, an isoquinolyl group, a phenanthridinyl group, an acridinyl group, a naphthyridinyl group, a quinoxalinyl group, a quinazolinyl group, a cinnolinyl group, a phthalazinyl group, a phenanthrolyl group, a phenazinyl group, a dibenzofuranyl group, a dibenzothiophenyl group, a carbazolyl group, a benzofuranyl group, a benzothiophenyl group, an indolyl group, cycloazyl group, a benzoimidazolyl group, a benzothiazolyl group, and benzothiadiazolyl group.

Of those substituents, a fused aromatic group which is tricyclic or more is preferable from the viewpoints of conductivity and a glass transition temperature, and a fused aromatic group which is tricyclic or more and is formed of a hydrocarbon is more preferable. This is because a fused aromatic group which is tricyclic or more and is formed of a hydrocarbon may reduce the uptake of an ionic impurity to a larger extent than that in the case of a fused polycyclic ring containing a hetero atom having a lone pair of electrons, and an increase in lifetime of a light emitting device can be expected. The reason for the foregoing is that the inclusion of an ionic impurity is one possible cause for the deterioration of an electroluminescence device due to energization.

Among the substituents of an aryl group or a heterocylic group, examples of the halogen atom include fluorine, chlorine, bromine, and iodine.

Examples of the linear or branched alkyl group includes a methyl group, an ethyl group, a normal propyl group, an isopropyl group, an normal butyl group, a tertiary butyl group, an octyl group, a cyclohexyl group, a methoxy group, and a trifluoro group.

Examples of the substituted amino group include a dimethylamino group, a diethylamino group, a dibenzylamino group, a diphenylamino group, a ditolylamino group, and a dianisolylamino group.

Examples of the heterocyclic group and the aryl group which may have a substituent include a phenyl group, a biphenyl group, a terphenyl group, a fluorenyl group, a naphthyl group, a fluoranthenyl group, an anthryl group, a phenanthryl group, a pyrenyl group, a tetracenyl group, a pentacenyl group, a triphenylenyl group, a perylenyl group, a thienyl group, a pyrrolyl group, a pyridyl group, a pyrazyl group, a pyrimidyl group, a pyridazinyl group, a quinolyl group, an isoquinolyl group, a phenanthridinyl group, an acridinyl group, a naphthyridinyl group, a quinoxalinyl group, a quinazolinyl group, a cinnolinyl group, a phthalazinyl group, a phenanthrolyl group, a phenazinyl group, a dibenzofuranyl group, a dibenzothiophenyl group, a carbazolyl group, a benzofuranyl group, a benzothiophenyl group, an indolyl group, cycloazyl group, a benzoimidazolyl group, a benzothiazolyl group, and benzothiadiazolyl group.

In addition, examples of the fused ring aromatic group having 3 or more rings include a fluorenyl group, a pyrenyl group, a fluoranthenyl group, a benzofluoranthenyl group, a tetracenyl group, a pentacenyl group, a triphenylenyl group, a perylenyl group, a chrysenyl group, a phenanthroryl group, a carbazolyl group, a dibenzofuranyl group, a phenazinyl group, and an acridinyl group. Preferable examples thereof include a fluorenyl group, a pyrenyl group, a fluoranthenyl group, a benzofluoranthenyl group, a triphenylenyl group, a phenanthroryl group, and a carbazolyl group, and a fluorenyl group, a fluoranthenyl group, a benzofluoranthenyl group, a pyrenyl group, a triphenylenyl group, and a carbazolyl group are more preferable, and a fluorenyl group, a fluoranthenyl group, a benzofluoranthenyl group, and a pyrenyl group are still more preferable.

When a light emitting layer is formed of a carrier transportable host material and a guest, a main process for light emission includes the following several steps:

1. the transport of an electron or a hole in the light emitting layer;
2. the generation of an exciton of the host material;
3. the transfer of excitation energy between host material molecules; and
4. the movement of the excitation energy from the host material to the guest.

Desired energy movement in each step, and light emission occur in competition with various deactivation steps.

Needless to say, the light emission quantum efficiency of a light emission central material itself must be large in order that the luminous efficiency of an organic light emitting device may be improved. However, the efficiency with which energy movement between host molecules or between host and guest molecules can be performed is also of great concern. In addition, the deterioration of light emission due to energization is assumed to be related to a change in environment surrounding a light emitting material due to at least the light emission central material itself or a molecule around the light emission central material, though no causes for the deterioration have been revealed at present.

In view of the foregoing, the inventors of the present invention have made various studies. As a result, the inventors have found that a device using a compound represented by the general formula (1) as a host or guest for its light emitting layer emits light with high efficiency, keeps high luminance for a long time period, and shows small deterioration of light emission due to energization.

One possible cause for the deterioration of the light emission due to the energization is the deterioration of the thin-film shape of the light emitting layer. The deterioration of the thin-film shape may result from the crystallization of the organic thin film due to, for example, the temperature of an environment in which the device is driven or heat generation at the time of the driving of the device. The crystallization may originate from the low glass transition temperature of a material for the thin film, so it is desired that an organic EL material have a high glass transition temperature. An improvement in durability of an organic EL device can be expected from the compound represented by the general formula (1) of the present invention because the compound has a high glass transition temperature.

The compound of the present invention has, in a fluoranthene skeleton, at least two identical fused polycyclic aromatic groups each of which: is represented by the general formula (2); is tricyclic or more; and has at least one fused ring structure at a position adjacent to a position at which a fluoranthene ring is substituted by the group.

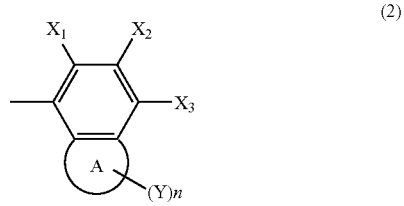

(2)

A ring structure A is preferably a four-, five-, six-, seven-, or eight-membered ring, and is more preferably a five- or six-membered ring from the viewpoint of structural stability.

The following effects can be expected from the introduction of two substituents each of which is tricyclic or more. First, an increase in glass transition temperature can be expected because of the following items (1) and (2): (1) an increase in glass transition temperature can be expected from an effect exerted by an increase in molecular weight of the compound and (2) the fact that ring structures are not coupled (like, for example, tetraphenylene) but turned into a fused polycyclic ring (pyrene) reduces the number of sites each showing a rotational motion in a molecule of the compound and makes the molecule additionally rigid, so the maintenance of a high glass transition temperature can be expected.

In addition, the molecular skeleton of the compound becomes rigid, so a molecular motion in an excited state can be expected to be small, and the compound can be expected to have high light emission quantum efficiency.

Further, a ring structure having a large π conjugate surface is generally considered to act advantageously on the conveyance of charge (carrier), so the compound of the present invention having two large fused polycyclic rings each of which is tricyclic or more is expected to act additionally advantageously on the transport of a carrier.

A state where those fused polycyclic aromatic groups each of which is tricyclic or more are identical to each other can reduce the number of steps of the synthesis of, and simplify synthesis and purification processes for, the compound as compared to the case where two different fused polycyclic aromatic groups each of which is tricyclic or more are introduced.

In addition, as represented by the general formula (2), a fused polycyclic aromatic ring which is tricyclic or more has a fused ring at a position adjacent to a position at which the group is bonded to a fluoranthene ring. An effect that can be expected from such structure is as follows: the ring structure A serves as steric hindrance to the fluoranthene ring to expand additionally an angle of twist between two rings, that is, the fluoranthene ring and the fused polycyclic aromatic ring which is tricyclic or more. The effect reduces the ease with which the crystallization of the compound from a glass state occurs, so an organic film having high stability may be obtained.

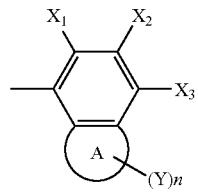

(2)

In addition, a large twist between the fused polycyclic ring which is tricyclic or more and the fluoranthene ring may prevent the fused polycyclic ring which is tricyclic or more and the conjugated system of the fluoranthene ring from linking with each other. As a result, when fluoranthene is mainly responsible for light emission, strong blue light derived from fluoranthene can be emitted.

In addition, a site of fluoranthene to which a substituent is introduced is preferably $R_3$ or $R_8$ in the general formula (1). $R_3$ corresponds to the peri position of $R_4$. When a substituent is introduced to the site, steric repulsion with the peri position occurs, and the fused polycyclic aromatic ring which is tricyclic or more may be introduced while largely twisting from the plane surface of the fluoranthene ring. A twist between the two rings makes a molecule of the compound sterically bulky, so a reducing effect on the crystallinity of the molecule can be expected. The effect reduces the ease with which the crystallization of the compound from a glass state occurs, so an organic film having high stability may be obtained.

In addition, among the substituents that can be introduced to the fluoranthene skeleton, the substituent most distant from the position of $R_3$ is placed at the position of $R_8$. The introduction of a sterically bulky substituent (such as a substituent having a peri position) to the position of $R_8$ is expected to exert a sterically shielding effect on the fluoranthene ring when the fluoranthene ring is mainly responsible for light emission. As a result, a phenomenon in which luminous efficiency reduces with increasing guest material concentration in a host material (referred to as "concentration quenching"), the phenomenon being often observed in a light emitting layer of an organic electroluminescence device, and the phenomenon becoming a problem in the case of the formation of a host-guest-based light emitting layer, can be suppressed. Accordingly, the concentration at which a light emitting material is dispersed in a host material can be increased, and a light emitting device having a high concentration of the light emitting material and high luminous efficiency can be realized.

Because of the above-mentioned effects, the organic electroluminescence device of the present invention having an organic layer formed by using such organic light emitting material shows excellent durability of the organic layer when the device is driven for a long time period.

Hereinafter, the specific structural formulae of organic compounds to be used in the present invention are shown below.
It should be noted that the formulae are merely representative examples, and the present invention is not limited to them.
XA-1
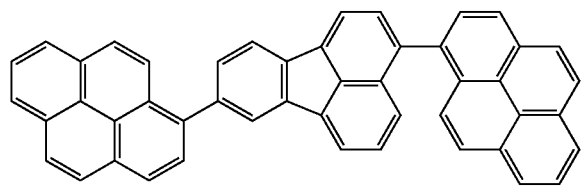
XA-2
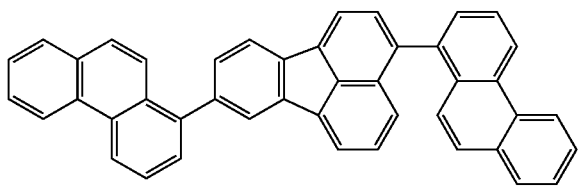
XA-3
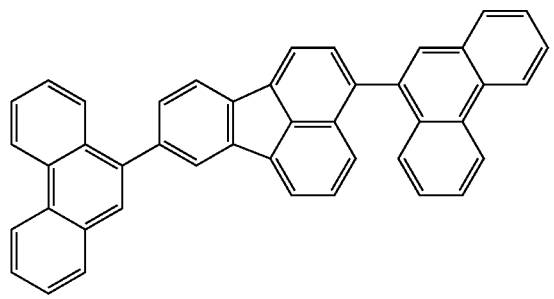
XA-4
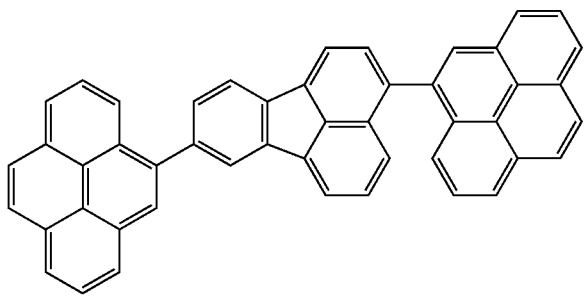
XA-5
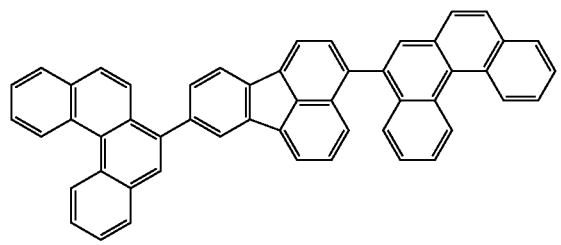
XA-6
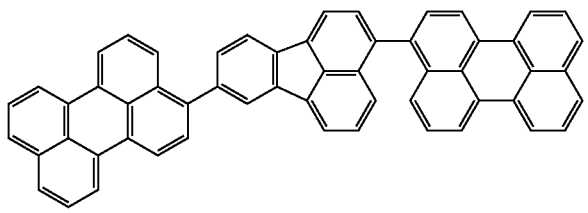
XA-7
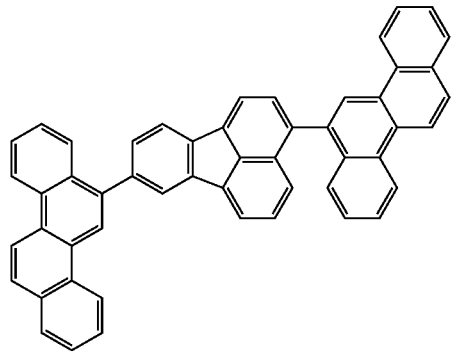
XA-8
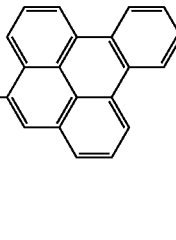
XA-9
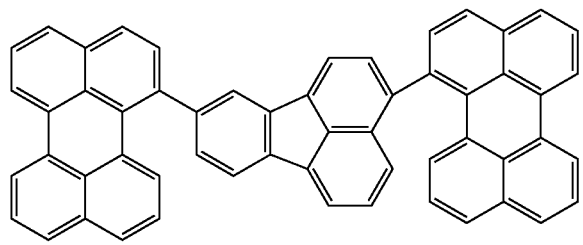
XA-10
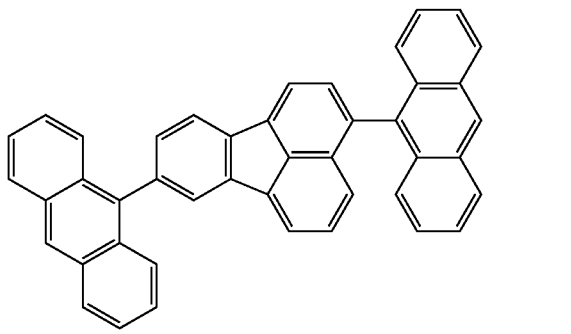

XA-11
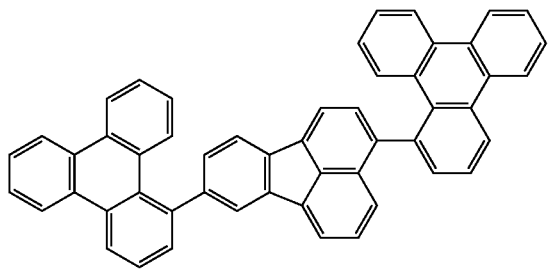
XA-12
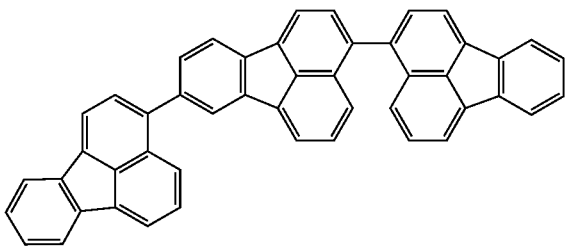
XA-13
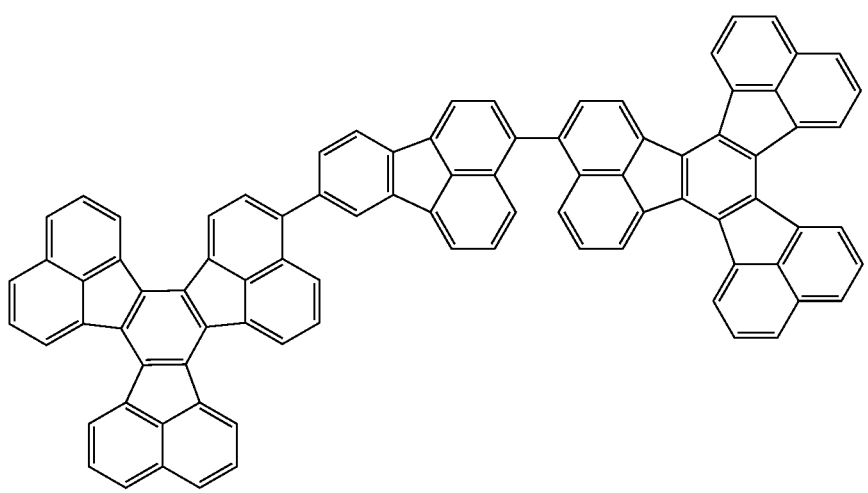
XA-14
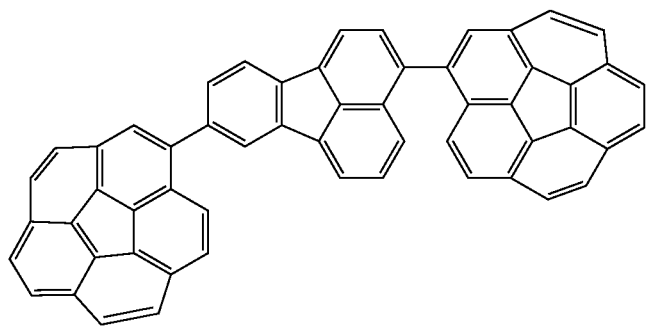
XA-15
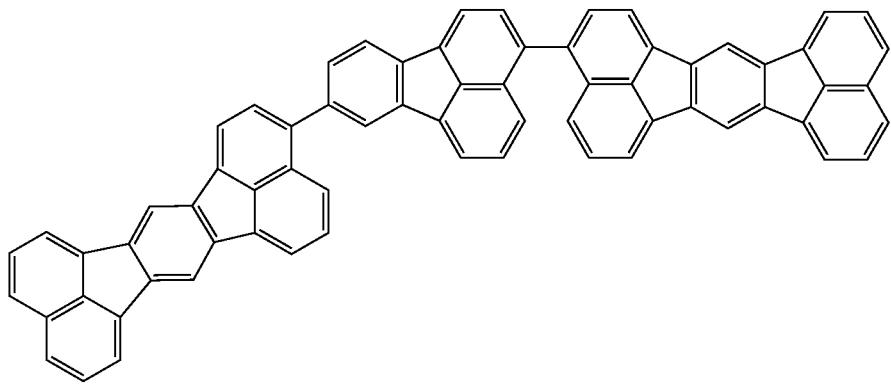

-continued
XA-16
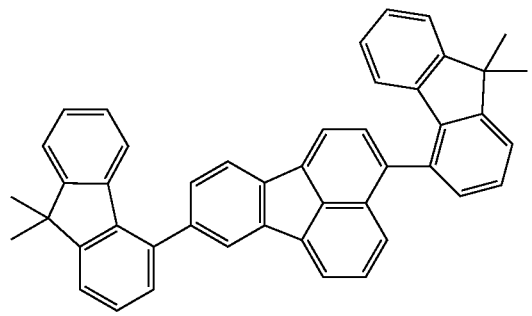
XA-17
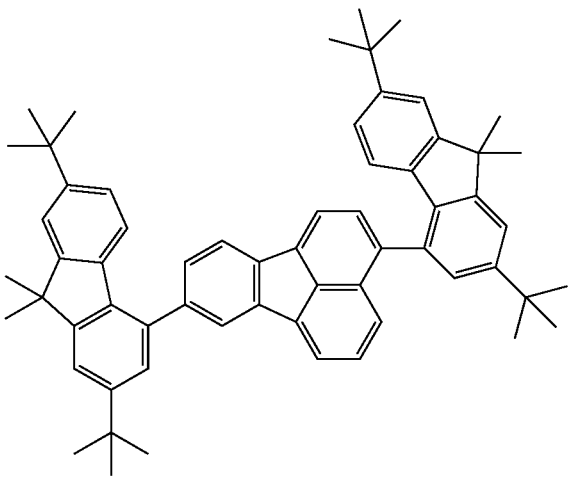
XA-18
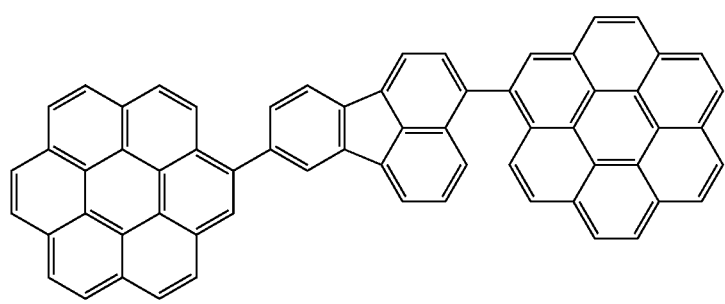
XA-19
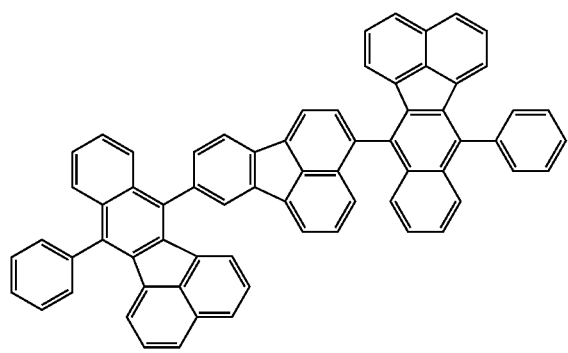
XA-20
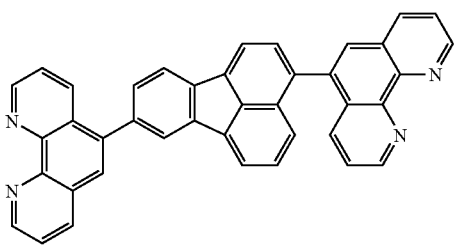
XA-21
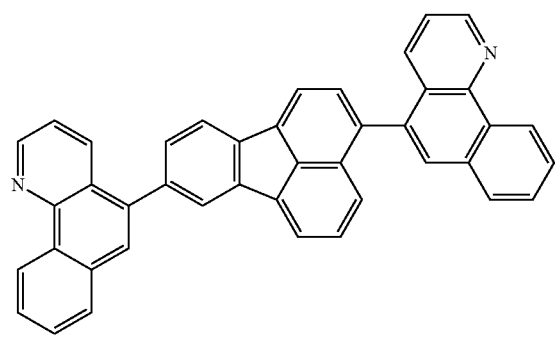
XA-22
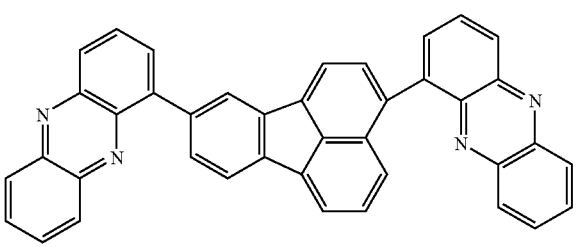

-continued
XA-23
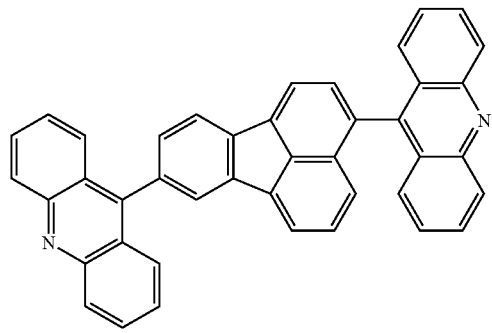
XA-24
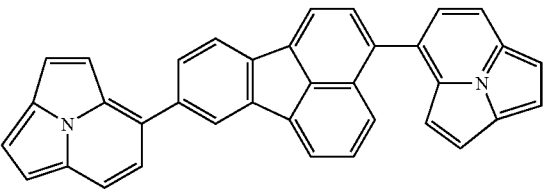
XA-25
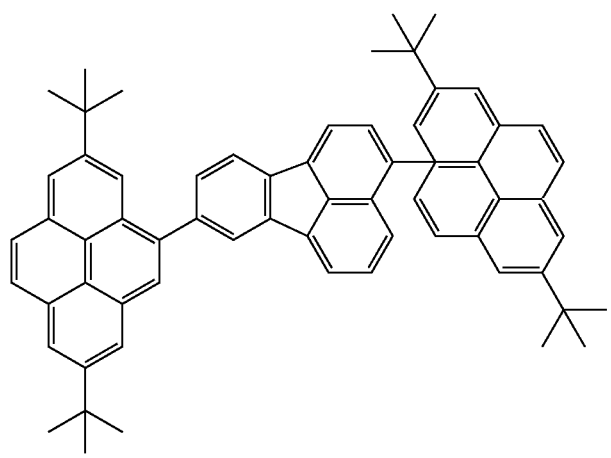
XA-26
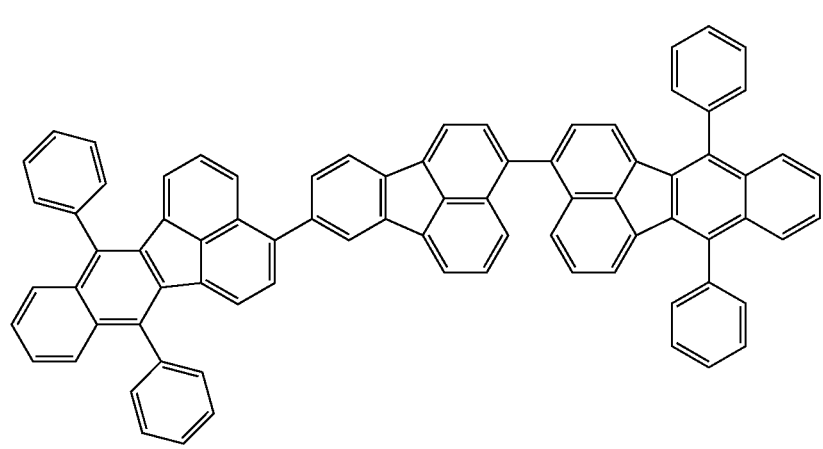
XA-27
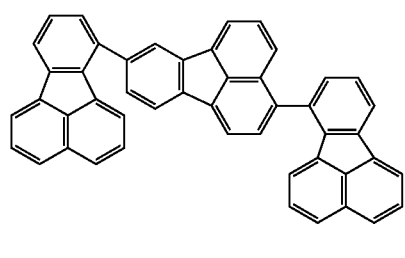
XA-28
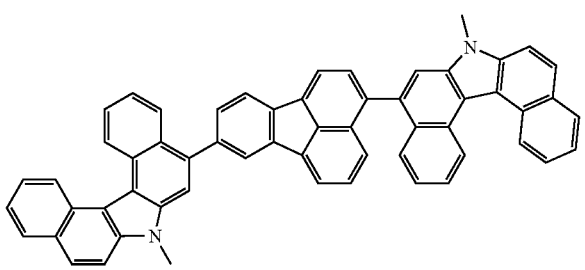

-continued
XA-29
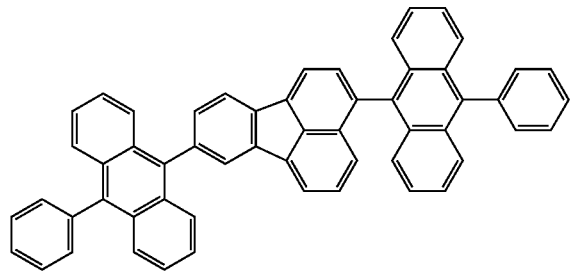
XA-30
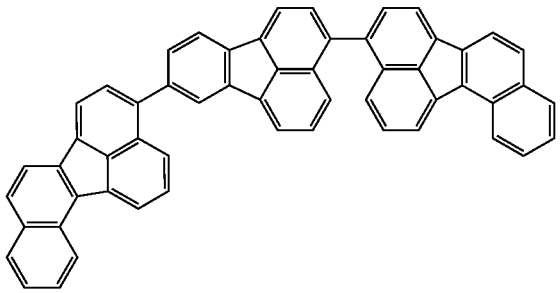
XA-31
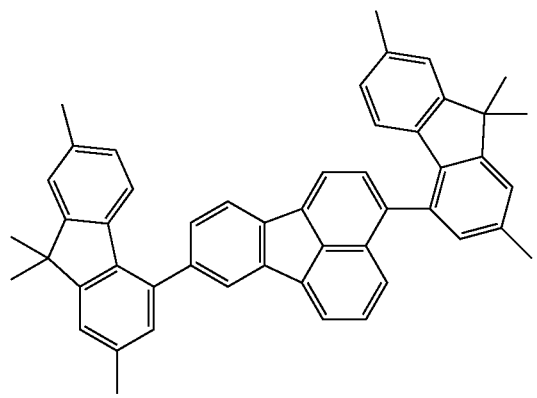
XA-32
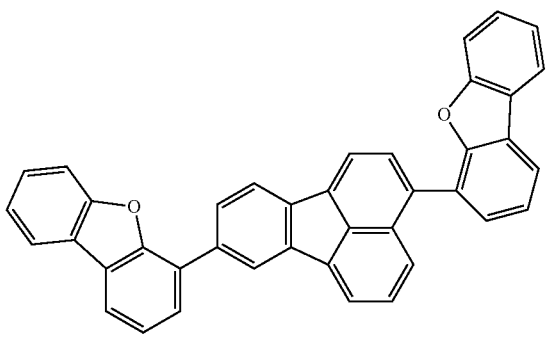
XA-33
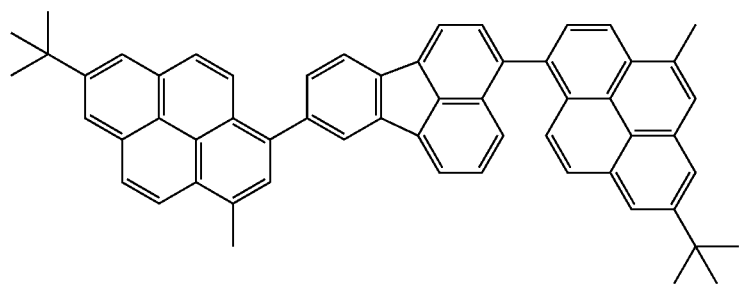
XA-34
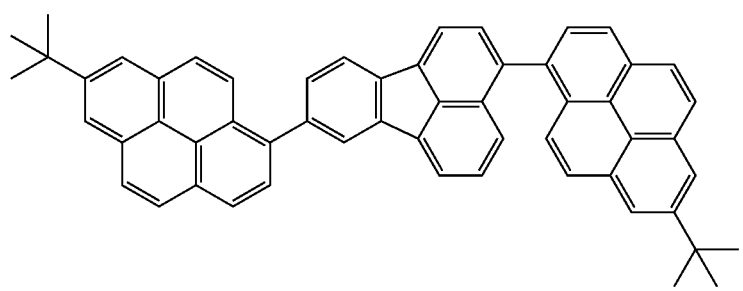

XA-36
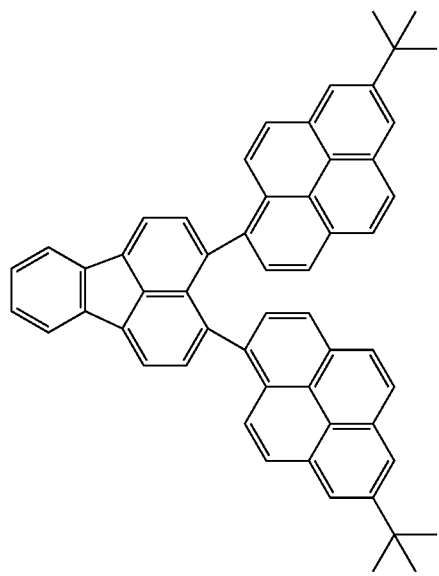
XA-37
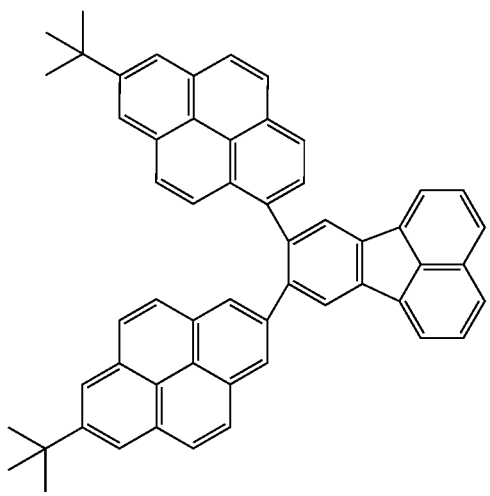
XA-38
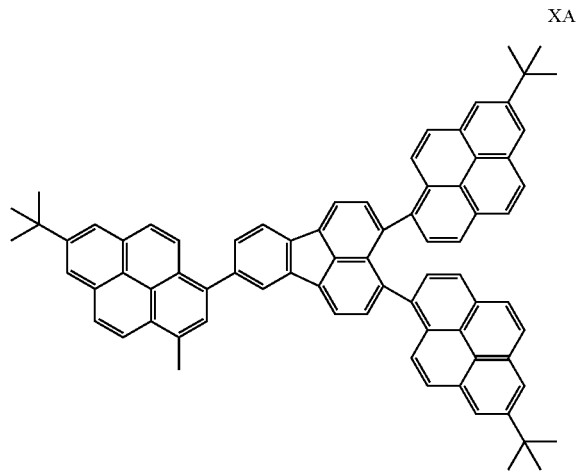
XA-39
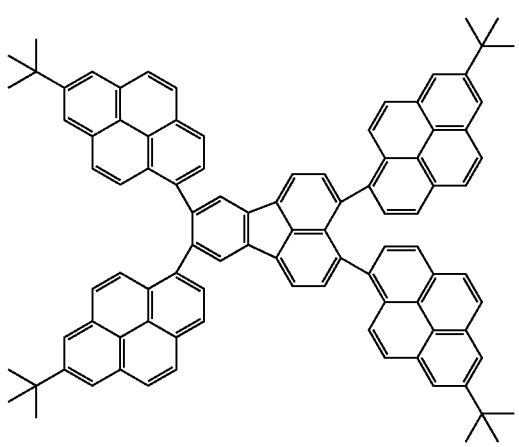
XA-40
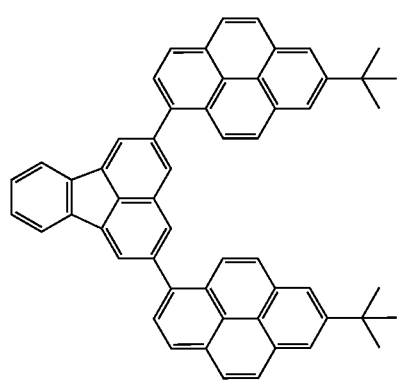
XA-41
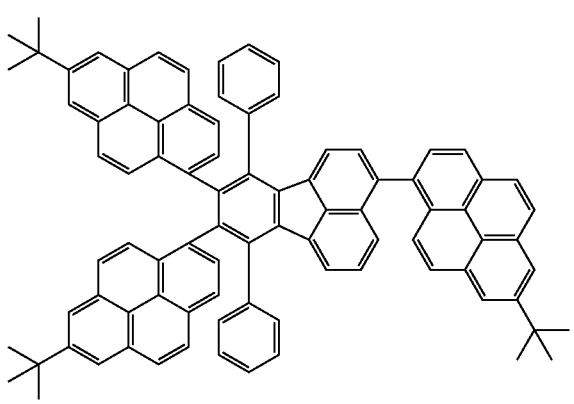

-continued
XA-42
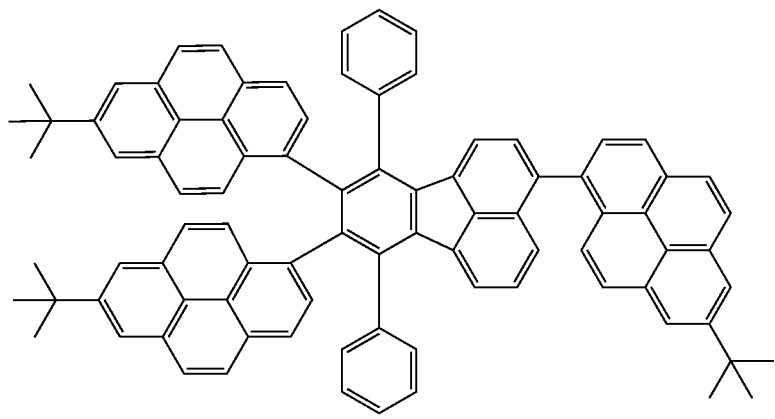
XA-43
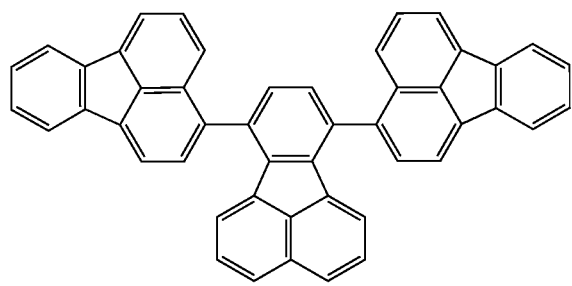
XA-44
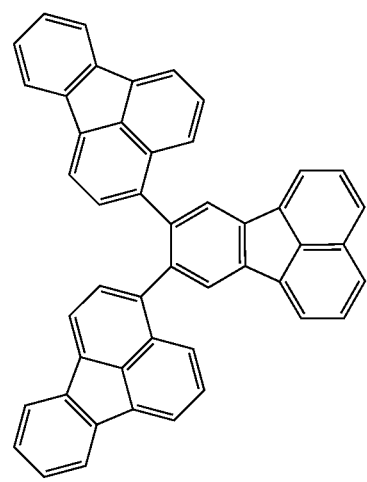
XA-45
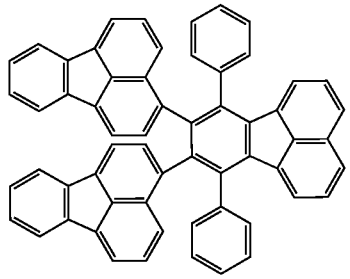
XA-46
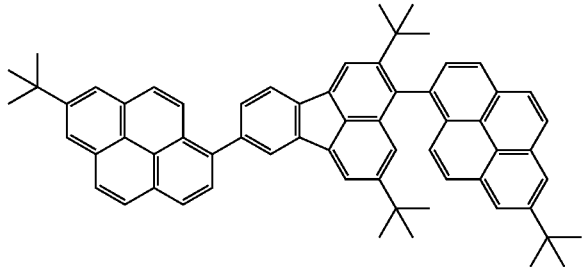
XA-47
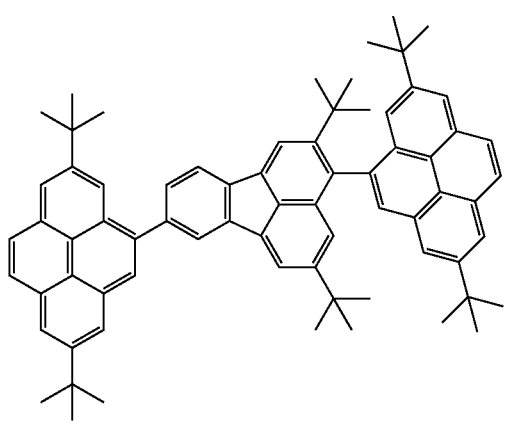
XA-48
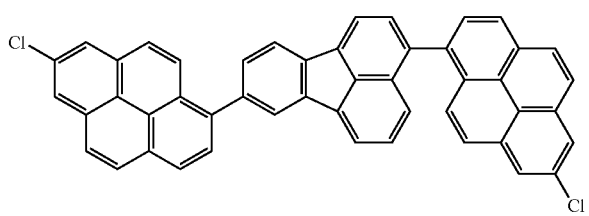

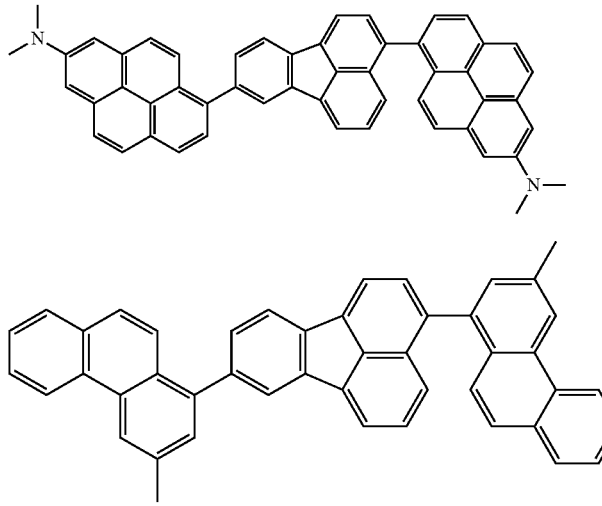

Next, the organic light emitting device of the present invention is described in detail.

The organic light emitting device of the present invention includes at least a pair of electrode including an anode and a cathode, and at least one layer held between the pair of electrode and containing an organic compound. In the organic light emitting device, the at least one layer containing an organic compound layer contains at least one compound represented by the general formula (1).

At least a light emitting layer among the layers each containing an organic compound of the organic light emitting device of the present invention preferably contains at least one kind of the compound represented by the general formula (1). In addition, in an organic light emitting device having a light emitting layer formed of two or more compounds including a host and a guest, the host or the guest is preferably the compound represented by the general formula (1). The term "guest" as used in the present invention refers to a compound that mainly emits light in response to recombination between a hole and an electron in the light emitting region of the organic EL device. The guest is incorporated into another compound (host) of which the light emitting region is formed.

The content of the compound represented by the general formula (1) according to the present invention to be used as the guest is preferably 50 wt % or less, more preferably 0.1 wt % or more to 30 wt % or less, or particularly preferably 0.1 wt % or more to 15 wt % or less.

On the other hand, when the compound represented by the general formula (1) according to the present invention is used as a host compound, the guest is not particularly limited, and, for example, a compound to be described later can be appropriately used depending on, for example, a desired luminescent color. In addition, the light emitting layer may be doped with a hole transportable compound or an electron transportable compound as required together with the guest.

The compound of the present invention, which may be used only in the light emitting layer among the organic compound layers, can be used in, a layer such as a hole injecting layer, a hole transporting layer, an electron injecting layer, an electron transporting layer, or an electron barrier layer in addition to the light emitting layer as required.

In the organic light emitting device of the present invention, the compound represented by the above general formula (1) is formed between the anode and the cathode by a vacuum vapor deposition method or a solution coating method. The thickness of the organic layer is smaller than 10 µm, preferably 0.5 µm or less, or more preferably 0.01 µm or more to 0.5 µm or less.

FIGS. 1 to 6 each show a preferable example of the organic light emitting device of the present invention.

First, reference numerals in the drawings are described.

Provided are a substrate 1, an anode 2, a light emitting layer 3, a cathode 4, a hole transporting layer 5, an electron transporting layer 6, a hole injecting layer 7, and a hole/exciton blocking layer 8.

FIG. 1 is a sectional view showing an example of an organic light emitting device according to the present invention. As shown in FIG. 1, the organic light emitting device has a structure in which the anode 2, the light emitting layer 3, and the cathode 4 are provided on the substrate 1 in this order. In this example, the light emitting device including a compound having all of hole-transporting property, electron-transporting property, and light-emitting property or including compounds having the respective properties in combination, is useful.

Figure 2:
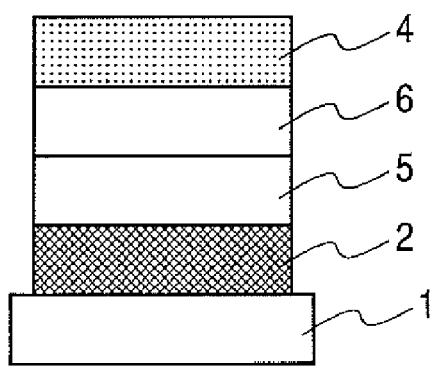
FIG. 2 is a sectional view showing another example of the organic light emitting device in the present invention.

FIG. 2 is a sectional view showing another example of the organic light emitting device according to the present invention. As shown in FIG. 2, the organic light emitting device has a structure in which the anode 2, the hole transporting layer 5, the electron transporting layer 6, and the cathode 4 are provided on the substrate 1 in this order. In this example, the following case is useful. That is, a light-emitting substance whose material has at least one of hole-transporting property and electron-transporting property is used for each layer, and the light-emitting substance is used in combination with a non-illuminant hole-transporting substance or electron-transporting substance. In this case, the light emitting layer 3 is formed of the hole transporting layer 5 or the electron transporting layer 6.

Figure 3:
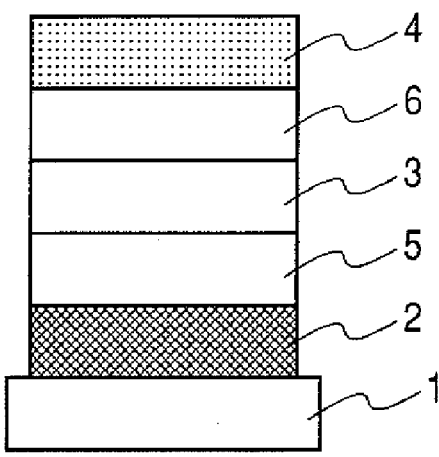
FIG. 3 is a sectional view showing another example of the organic light emitting device in the present invention.

FIG. 3 is a sectional view showing still another example of the organic light emitting device according to the present invention. As shown in FIG. 3, the organic light emitting device has a structure in which the anode 2, the hole transporting layer 5, the light emitting layer 3, the electron transporting layer 6, and the cathode 4 are provided on the substrate 1 in this order. This organic light emitting device has separate carrier-transporting function and light-emitting function. Further, compounds each having hole-transporting property, electron-transporting property, or light-emitting property are used in combination as appropriate, thereby allowing a substantial increase in freedom of choice in material to be used. In addition, various compounds having different light emission wavelengths can be used, thereby allowing an increase in variety of luminescent colors.

Further, luminous efficiency may be improved by efficiently trapping each carrier or exciton in the light emitting layer provided in the middle of the device.

Figure 4:
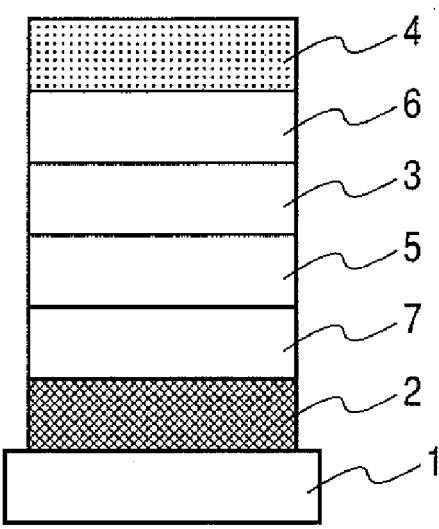
FIG. 4 is a sectional view showing another example of the organic light emitting device in the present invention.

FIG. 4 is a sectional view showing yet another example of the organic light emitting device according to the present invention. The organic light emitting device of FIG. 4 has a structure shown in FIG. 3 except that the hole-injecting layer 7 is inserted into a side of the anode. This structure is effective for improving adhesiveness between the anode and the hole transporting layer or for improving hole-injecting property, which is effective in lowering a voltage to be applied to the device.

Figure 5:
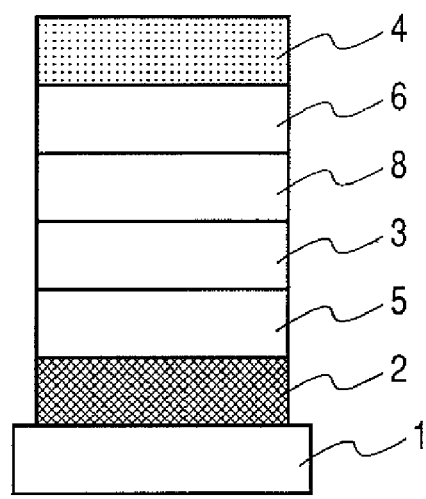
FIG. 5 is a sectional view showing another example of the organic light emitting device in the present invention.
Figure 6:
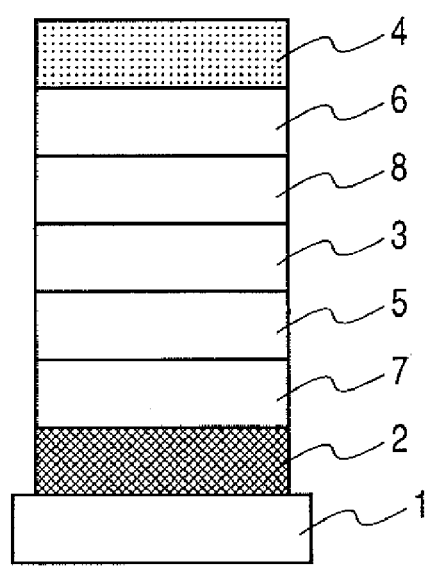
FIG. 6 is a sectional view showing another example of the organic light emitting device in the present invention.

Each of FIGS. 5 and 6 is a sectional view showing still yet another example of the organic light emitting device according to the present invention. The organic light emitting device of FIG. 5 has a structure shown in FIG. 3 except that a layer (the hole/exciton-blocking layer 8) for blocking travel of a hole or exciton to a side of the cathode is inserted between the light emitting layer and the electron transporting layer. Each of those structures uses a compound having an extremely high ionization potential for the hole/exciton-blocking layer 8 and is effective for improving luminous efficiency.

However, FIGS. 1 to 6 each show a basic device structure, and the structure of the organic light emitting device using the compound of the present invention is not limited to the structures described above. For example, the organic light emitting device of the present invention may have any one of various layer structures including: a structure having an insulating layer provided at an interface between the electrode and the organic layer; a structure having an adhesive or interference layer is provided; and a structure in which a hole transporting layer is composed of two layers with different ionization potentials.

The compound shown in the formula (1) of the present invention may be used for any one of the structures shown in FIGS. 1 to 6.

In the present invention, the compound represented by the general formula (1) is used as a constituent component for the light emitting layer. A conventionally known hole transportable compound, luminous compound or electron transportable compound can be used together with the compound as required.

In the organic light emitting device according to the present invention, the layer containing the compound shown in the formula (1) and layers containing other organic compounds are each formed by the following method. A thin film is generally formed by a vacuum vapor deposition method or a coating method in which a compound is dissolved in an appropriate solvent. In film formation by the coating method, in particular, a film may be formed by using a compound in combination with an appropriate binder resin.

The binder resin may be selected from a wide variety of binder resins. Examples of the binder resin include, but not limited to: a polyvinyl carbazole resin; a polycarbonate resin; a polyester resin; a polyallylate resin; a polystyrene resin; an acrylic resin; a methacrylic resin; a butyral resin; a polyvinyl acetal resin; a diallyl phthalate resin; a phenol resin; an epoxy resin; a silicone resin; a polysulfone resin; and a urea resin. One kind of binder resin may be used alone, or at least one kind thereof may be mixed and used as a copolymer.

An anode material may have as large a work function as possible, and examples thereof include: a metal element such as gold, platinum, nickel, palladium, cobalt, selenium, or vanadium; an alloy thereof; and a metal oxide such as tin oxide, zinc oxide, indium tin oxide (ITO), or indium zinc oxide. Further, a conductive polymer such as polyaniline, polypyrrole, polythiophene, or polyphenylene sulfide may also be used. Each of those electrode materials may be used alone, or two or more kinds thereof may be used in combination.

Meanwhile, a cathode material may have a small work function, and examples thereof include: a metal element such as lithium, sodium, potassium, cesium, calcium, magnesium, aluminum, indium, silver, lead, tin, or chromium; and an alloy of two or more kinds thereof. A metal oxide such as indium tin oxide (ITO) may also be used. Further, the cathode may have a single layer structure or a multilayer structure.

The substrate to be used in the present invention is not particularly limited, but examples thereof include: an opaque substrate such as a metallic substrate or a ceramics substrate; and a transparent substrate such as a glass substrate, a quartz substrate, or a plastic sheet substrate. In addition, the substrate may have a color filter film, a fluorescent color converting filter film or a dielectric reflection film for controlling luminescent color.

Further, a protective layer or a sealing layer may be formed on the produced device to prevent contact between the device and oxygen or moisture. Examples of the protective layer include: a diamond thin film; a film formed of an inorganic material such as metal oxide or metal nitride; a polymer film formed of a fluorine resin, polyparaxylene, polyethylene, a silicone resin or a polystyrene resin; and a photo-curable resin. Further, the device itself may be covered with glass, an airtight film or a metal and packaged with an appropriate sealing resin.

Hereinafter, the present invention will be described more specifically by way of examples. However, the present invention is not limited to these examples.

EXAMPLE 1

Synthesis of Exemplified Compound No. XA-12

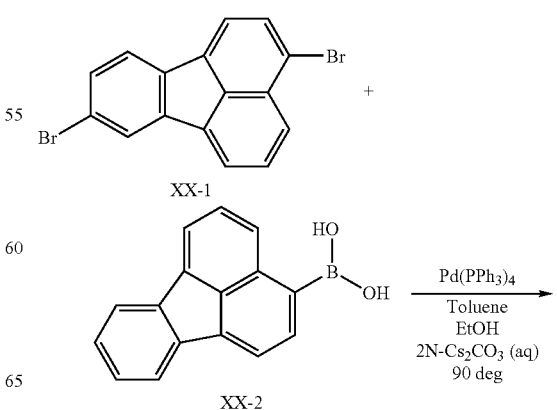

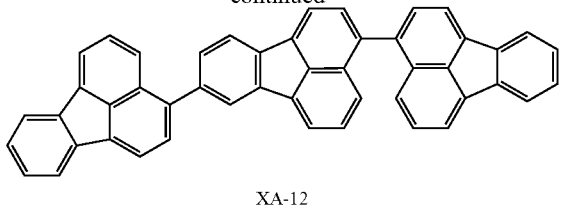

XA-12

XX-1 (500 mg, 1.39 mmol), XX-2 (754 mg, 3.06 mmol), toluene (20 mL), a 2N aqueous solution of cesium carbonate (20 mL), ethanol (10 mL), and tetrakistriphenylphosphine palladium[0] (161 mg, 0.139 mmol) were added to a 100-ml reaction vessel. The solution was heated to 90° C., and was stirred at the temperature for 10 hours. After the solution had been cooled to room temperature, the precipitated crystal was filtrated, whereby a coarse crystal was obtained. The coarse crystal was recrystallized from orthodichlorobenzene, whereby Exemplified Compound No. XA-12 as a target product was obtained (677 mg, 1.12 mmol, yield=81%).

Matrix-assisted laser desorption/ionization time-of-flight mass spectrometry (MALDI-TOF MS) confirmed that the compound had an M+ of 602.7.

In this compound, the peri positions of fluoranthene molecules are bonded to each other at the $R_3$ position in the general formula (1), and the peri position of a fluoranthene molecule is bonded to a substituent at the $R_8$ position in the general formula (1). The light emission spectrum of Exemplified Compound No. XA-12 in a toluene solution had a λmax of 467 nm, and the observation of the light emission of blue light derived from fluoranthene was attained irrespective of the fact that this compound was a multiple body of large conjugated rings. The introduction of a sterically bulky substituent to the $R_3$ position or the $R_8$ position has an increasing effect on the molecular weight of this compound while maintaining the light emission of blue light.

EXAMPLE 2

Synthesis of Exemplified Compound No. XA-17

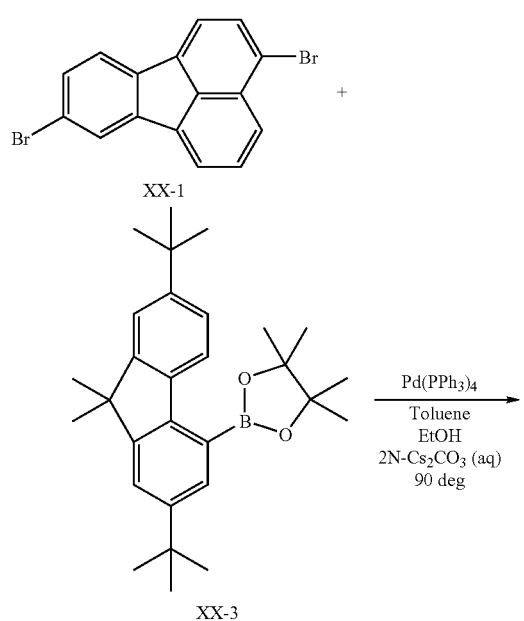

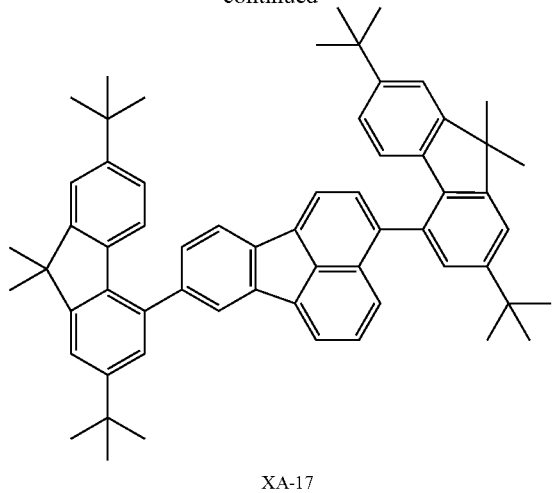

XA-17

XX-1 (500 mg, 1.39 mmol), XX-3 (1.28 g, 3.06 mmol), toluene (80 mL), an aqueous solution of cesium carbonate (containing 2 g of cesium carbonate and 15 mL of distilled water), ethanol (40 mL), and tetrakistriphenylphosphine palladium[0] (321 mg, 0.278 mmol) were added to a 200-ml reaction vessel. The solution was heated to 90° C., and was stirred at the temperature for 5 hours. After having been cooled to room temperature, the resultant was extracted with toluene (30 ml×three times), and an organic layer was dried with magnesium sulfate. The drying agent was filtrated, and the filtrate was condensed. After that, the residue was purified by means of silica gel column chromatography (mobile phase; toluene:heptane=1:3), whereby Exemplified Compound No. XA-17 as a target product was obtained (780 mg, 0.96 mmol, yield=69%).

Matrix-assisted laser desorption/ionization time-of-flight mass spectrometry (MALDI-TOF MS) confirmed that the compound had an M+ of 810.5.

In addition, NMR measurement identified the structure of the compound.

$^1$H NMR (CDCl$_3$, 400 MHz)σ (ppm): 8.10 (br, 3H), 7.93 (d, 1H, J=7.0 Hz), 7.73 (d, 1H, J=7.0 Hz), 7.62-7.33 (m, 9H), 7.11 (br, 1H), 7.02 (br, 1H), 6.84 (br, 1H), 6.38 (br, 1H), 1.60 (s, 3 H), 1.58 (s, 3H), 1.57 (br, 6H), 1.44 (s, 9H), 1.43 (s, 9H), 1.30 (br, 6H), 1.25 (br, 6H).

The light emission spectrum of Exemplified Compound No. XA-17 in a toluene solution was such that blue light having a λmax of 476 nm was emitted. An organic thin film formed only of Exemplified Compound No. XA-17 emitted blue light having a luminous wavelength of 478 nm, and no change in luminous wavelength was observed.

The introduction of two large substituents to a fluoranthene ring has a suppressing effect on concentration quenching.

EXAMPLE 3

As the anode, a film of indium tin oxide (ITO) having a thickness of 120 nm was formed on a glass substrate by a sputtering method, and the resultant was used as a transparent conductive supporting substrate. The resultant substrate was subjected to ultrasonic cleaning in acetone and isopropyl alcohol (IPA) in this order. Then, the substrate was washed in boiling IPA and dried. The substrate was further subjected to UV/ozone cleaning to be used as a transparent conductive supporting substrate.

The following organic layers and electrode layers were continuously formed on the transparent conductive supporting substrate by vacuum vapor deposition based on resistance heating in a vacuum chamber having a pressure of $10^{-5}$ Pa, whereby a device was produced.

Hole transporting layer (20 nm): Exemplified Compound No. XX-5

Light emitting layer (20 nm): Exemplified Compound No. XA-12 (5% in weight ratio): Compound XX-6

Electron transporting layer (30 nm): Bphen (manufactured by DOJINDO LABORATORIES)

Metal electrode layer 1 (0.5 nm): LiF

Metal electrode layer 2 (150 nm): Al

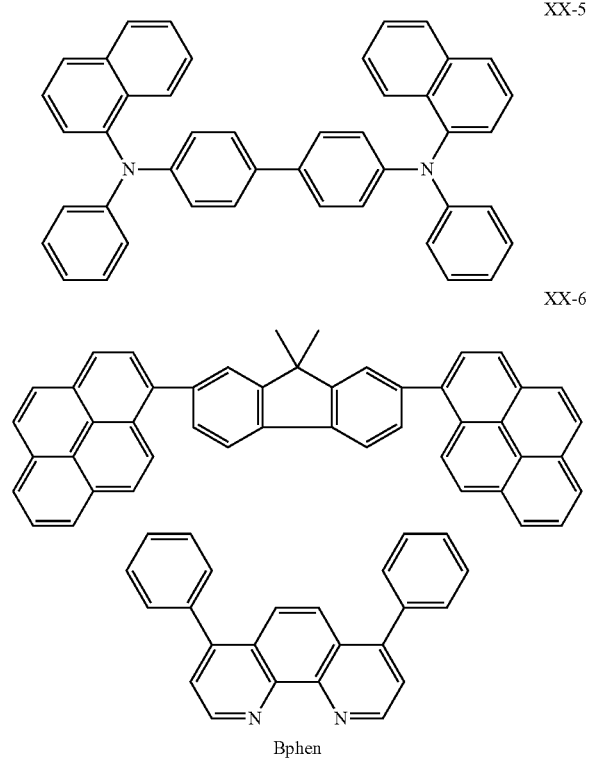

The current-voltage characteristics of the resultant EL device were measured with a microammeter 4140 B manufactured by Hewlett-Packard Development Company, and the light emission luminance of the device was measured with a BM 7 manufactured by TOPCON CORPORATION. Further, a voltage was applied to the device of the present invention for 100 hours under a nitrogen atmosphere. As a result, the device was observed to emit light in a favorable manner continuously.

EXAMPLE 4

A device was produced in the same manner as in Example 3 except that Exemplified Compound No. XA-17 was used instead of Exemplified Compound No. XA-12 of Example 2. A voltage was applied to the device of this example under a nitrogen atmosphere for 100 hours. As a result, the device was observed to emit good light continuously.

EXAMPLE 5

Synthesis of Exemplified Compound No. XA-3

Exemplified Compound No. XA-3 can be synthesized in the same manner as in Example 2 except that XX-7 is used instead of XX-3 of Example 2.

EXAMPLE 6

Synthesis of Exemplified Compound No. XA-4

Exemplified Compound No. XA-4 can be synthesized in the same manner as in Example 2 except that XX-8 is used instead of XX-3 of Example 2.

EXAMPLE 7

Synthesis of Exemplified Compound No. XA-6

Exemplified Compound No. XA-6 can be synthesized in the same manner as in Example 2 except that XX-9 is used instead of XX-3 of Example 2.

EXAMPLE 8

Synthesis of Exemplified Compound No. XA-7

Exemplified Compound No. XA-7 can be synthesized in the same manner as in Example 2 except that XX-10 is used instead of XX-3 of Example 2.

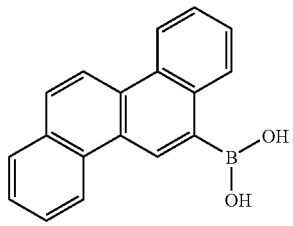
XX-10

EXAMPLE 9

Synthesis of Exemplified Compound No. XA-14

Exemplified Compound No. XA-14 can be synthesized in the same manner as in Example 2 except that XX-11 is used instead of XX-3 of Example 2.

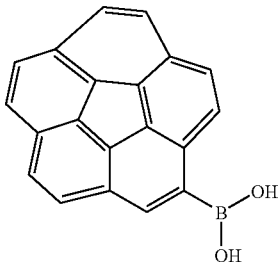
XX-11

EXAMPLE 10

Synthesis of Exemplified Compound No. XA-19

Exemplified Compound No. XA-19 can be synthesized in the same manner as in Example 2 except that XX-12 is used instead of XX-3 of Example 2.

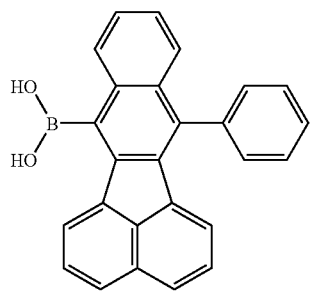
XX-12

EXAMPLE 11

Synthesis of Exemplified Compound No. XA-20

Exemplified Compound No. XA-20 can be synthesized in the same manner as in Example 2 except that XX-13 is used instead of XX-1 of Example 2 and XX-14 is used instead of XX-3 of Example 3.

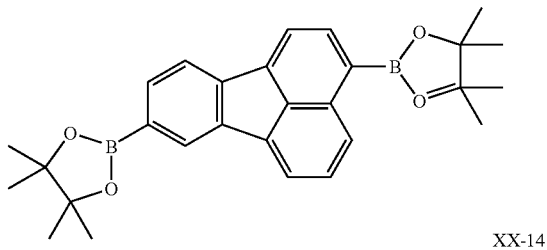
XX-13

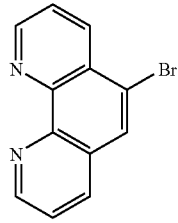
XX-14

EXAMPLE 12

Synthesis of Exemplified Compound No. XA-25

Exemplified Compound No. XA-25 can be synthesized in the same manner as in Example 2 except that XX-15 is used instead of XX-3 of Example 2.

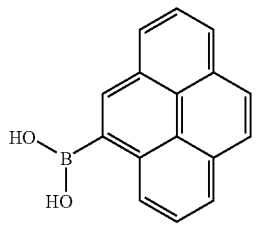
XX-15

This application claims the benefit of Japanese Patent Application No. 2006-123783, filed Apr. 27, 2006, and No. 2007-042663, filed Feb. 22, 2007 which are hereby incorporated by reference herein in their entirety.

The invention claimed is:

1. A fluoranthene derivative compound represented by the following formula:

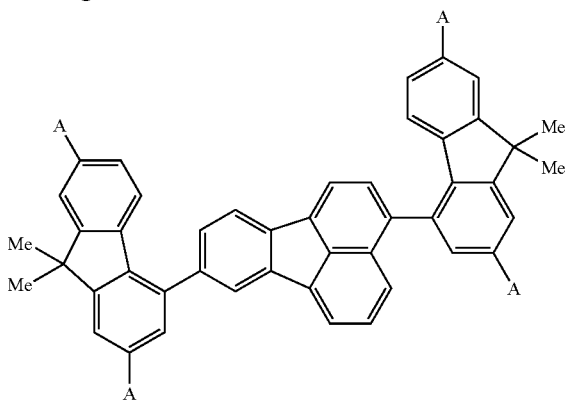

wherein A is a linear or branched alkyl group and each A represents the same group.

2. An organic light emitting device comprising:
an anode;
a cathode; and
an organic compound layer interposed between the anode and the cathode,
wherein the organic compound layer comprises the fluoranthene derivative according to claim 1.

3. The organic light emitting device according to claim 2, wherein the organic compound layer comprises a light emitting layer.

4. The organic light emitting device according to claim 2, wherein the organic light emitting device comprises an electroluminescence device that emits light by applying a voltage between the anode and the cathode.

5. The organic light emitting device according to claim 3, wherein the light emitting layer comprises a host material and a guest material, wherein said guest material is represented by the following formula:

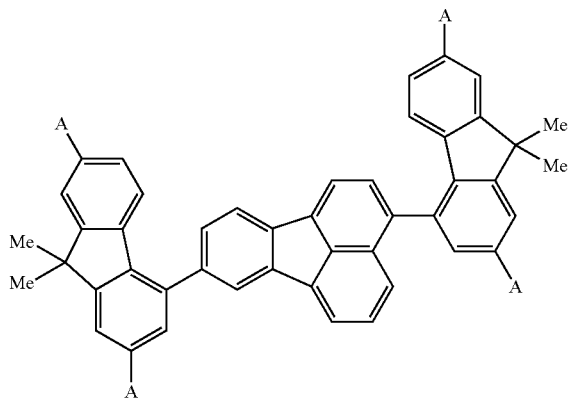

wherein A is a linear or branched alkyl group and each A represents the same group.

6. The organic light emitting device according to claim 5, wherein said host material is represented by the following formula:

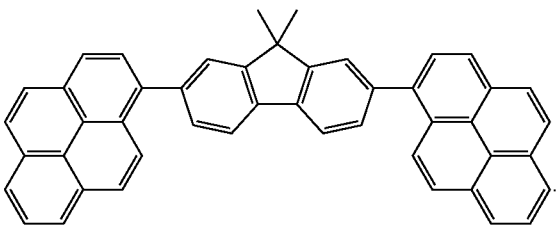

* * * * *